(12) United States Patent
Dross (10) Patent No.: US 9,044,222 B2
(45) Date of Patent: Jun. 2, 2015

(54) ARTHROSCOPIC METHOD AND APPARATUS FOR TISSUE ATTACHMENT TO BONE

(75) Inventor: Brian Dross, Mt. Pleasant, SC (US)

(73) Assignee: Microaire Surgical Instruments, LLC, Charlottesville, VA (US)

( * ) Notice: Subject to any disclaimer, the term of this patent is extended or adjusted under 35 U.S.C. 154(b) by 46 days.

(21) Appl. No.: 13/490,003

(22) Filed: Jun. 6, 2012

(65) Prior Publication Data

US 2012/0323248 A1      Dec. 20, 2012

Related U.S. Application Data

(60) Division of application No. 11/954,612, filed on Dec. 12, 2007, now Pat. No. 8,282,643, which is a continuation-in-part of application No. 11/157,631, filed on Jun. 21, 2005, now abandoned.

(51) Int. Cl.
*A61B 17/17* (2006.01)
*A61B 17/04* (2006.01)
*A61B 17/16* (2006.01)
*A61B 17/06* (2006.01)

(52) U.S. Cl.
CPC ......... *A61B 17/0487* (2013.01); *A61B 17/1714* (2013.01); *A61B 17/17* (2013.01); *A61B 17/0483* (2013.01); *A61B 17/0485* (2013.01); *A61B 17/1642* (2013.01); *A61B 17/1684* (2013.01); *A61B 17/1796* (2013.01); *A61B 2017/06028* (2013.01); *A61B 2017/0608* (2013.01); *A61B 2017/1778* (2013.01)

(58) Field of Classification Search
USPC ............. 606/300–304, 74, 323, 102, 104, 80, 606/139, 148, 149, 86 R–89, 96–98, 606/96 R–98
See application file for complete search history.

(56) References Cited

U.S. PATENT DOCUMENTS

| | | | |
|---|---|---|---|
| 4,541,423 A | | 9/1985 | Barber |
| 4,722,331 A | * | 2/1988 | Fox .................................. 606/96 |
| 4,744,353 A | | 5/1988 | McFarland |
| 4,941,466 A | | 7/1990 | Romano |
| 4,945,904 A | * | 8/1990 | Bolton et al. .................... 606/96 |
| 5,330,468 A | | 7/1994 | Burkhart |
| 5,562,664 A | * | 10/1996 | Durlacher et al. ............... 606/96 |
| 5,575,801 A | | 11/1996 | Habermeyer et al. |
| 5,681,333 A | * | 10/1997 | Burkhart et al. ............... 606/148 |
| 5,840,078 A | | 11/1998 | Yerys |
| 6,059,789 A | | 5/2000 | Dinger et al. |
| 6,132,433 A | | 10/2000 | Whelan |

(Continued)

FOREIGN PATENT DOCUMENTS

| | | |
|---|---|---|
| DE | 3411891 A1 | 10/1985 |
| EP | 0081857 | 6/1983 |
| WO | WO 0067651 | 11/2000 |

*Primary Examiner* — David Bates
*Assistant Examiner* — Michael Araj
(74) *Attorney, Agent, or Firm* — Whitham Curtis Christofferson & Cook, PC (57) ABSTRACT

Methods are described wherein bone constructs of a patient are used to arthroscopically attach sutures to torn or dysfunctional tissue. A suture or multiple sutures are passed through intersecting/bisecting tunnels formed in the bone. An end of the suture extends from each of the tunnels, and the ends are used to secure the tissue to the bone, such as by arthroscopic tying of the ends, and pulling the tissue against the bone. Devices for performing the methods are also described.

10 Claims, 10 Drawing Sheets

(56) References Cited

U.S. PATENT DOCUMENTS

| | | |
|---|---|---|
| 6,187,011 B1 * | 2/2001 | Torrie ............... 606/96 |
| 6,238,400 B1 | 5/2001 | Bays |
| 6,267,766 B1 | 7/2001 | Burkhart |
| 6,379,364 B1 * | 4/2002 | Brace et al. ............ 606/96 |
| 6,524,317 B1 | 2/2003 | Ritchart et al. |
| 6,540,750 B2 | 4/2003 | Burkhart |
| 6,582,453 B1 | 6/2003 | Tran et al. |
| 6,592,609 B1 | 7/2003 | Bonutti |
| 6,692,516 B2 | 2/2004 | West, Jr. et al. |
| 6,770,076 B2 | 8/2004 | Foerster |
| 6,884,249 B2 * | 4/2005 | May et al. ............ 606/148 |
| 6,991,636 B2 | 1/2006 | Rose |
| 7,503,920 B2 * | 3/2009 | Siegal ............... 606/79 |
| 7,569,059 B2 | 8/2009 | Cerundolo |
| 7,771,441 B2 | 8/2010 | Cerundolo |
| 7,833,230 B2 | 11/2010 | Cerundolo |
| 7,833,244 B2 | 11/2010 | Cerundolo |
| 2003/0050642 A1 | 3/2003 | Schmieding |
| 2004/0186482 A1 * | 9/2004 | Kolb et al. ............ 606/96 |
| 2004/0236373 A1 | 11/2004 | Anspach, III |

* cited by examiner

ARTHROSCOPIC METHOD AND APPARATUS FOR TISSUE ATTACHMENT TO BONE

CROSS-REFERENCE TO RELATED APPLICATIONS

This application is a division of application Ser. No. 11/954,612 filed Dec. 12, 2007, now U.S. Pat. No. 8,282,643 which issued Oct. 9, 2012, which is a continuation-in-part of application Ser. No. 11/157,631 filed on Jun. 21, 2005 now abandoned, on which the present application is based and benefit claimed under 35 U.S.C. §119(e), is incorporated herein by reference.

BACKGROUND OF THE INVENTION

1. Field of the Invention

The invention relates to methods and devices for the arthroscopic fixation of tissue to bone using sutures. More specifically, this invention relates to a method and device for delivering sutures through bone.

2. Description of the Prior Art

Invasive and open surgery methods of attachment of tissue to bone to repair tissue is known and used. Furthermore, it is common practice to provide a passageway in a bone to reattach a torn or separated tendon to the bone. In some repair processes, foreign objects, such as suture anchors, staples or screws, are implanted and used to connect tissue to bone. An example of this method is rotator cuff surgery where the tendon may be detached or partially torn from the humerous. Thus, there is a need to overcome the invasive nature of tissue repairs by open surgical processes, and reduce the reliance on implants associated with arthroscopic repairs.

SUMMARY OF THE INVENTION

The present invention uses the bone constructs of the patient to attach sutures to torn or dysfunctional tissue. A first tunnel is arthroscopically formed in a bone. A second tunnel is arthroscopically made in the same bone and is directed to intersect/bisect the first tunnel. A suture or multiple sutures are passed through intersecting/bisecting tunnels and an end of the suture extends from each of the tunnels. The ends are used to secure the tissue to the bone, such as by arthroscopic tying of the ends, and pulling the tissue against the bone. In one aspect of the invention one of the tunnels is not linear, e.g., is curved as it passes to the intersection/bisection of the tunnels. In a preferred embodiment of the invention a suture stylus is provided for pushing sutures and knots. Another aspect of this invention is to provide an apparatus for maintaining the drill guides for each tunnel in a precise relationship so that the tunnels will be accurately placed.

BRIEF DESCRIPTION OF THE DRAWINGS

Having described the invention in general terms, reference will now be made to the accompanying drawings, which are not necessarily drawn to scale, and wherein.

DETAILED DESCRIPTION OF THE PREFERRED EMBODIMENT

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be through and complete, and will fully convey the scope of the invention to those skilled in the art.

Figure 2:
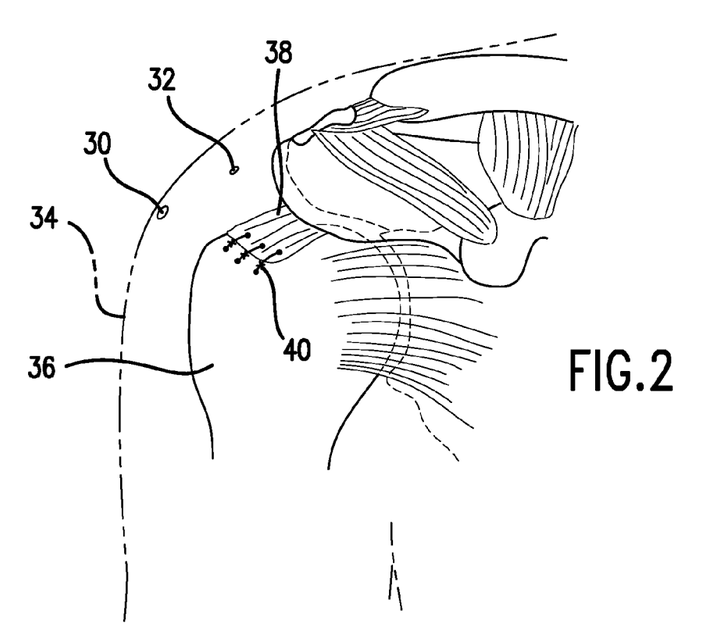
FIG. 2 illustrates three arthroscopic simple stitches, a repaired rotator cuff, and two lateral vertical portals.
Figure 3:
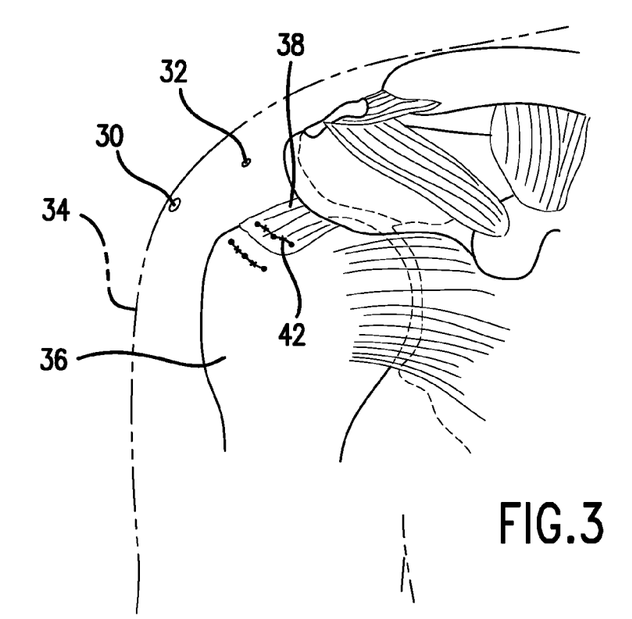
FIG. 3 illustrates two arthroscopic mattress stitches where the suture material in the bone tunnel was positioned by a suture stylus or knot pusher and was used to pass two sutures.
Figure 5:
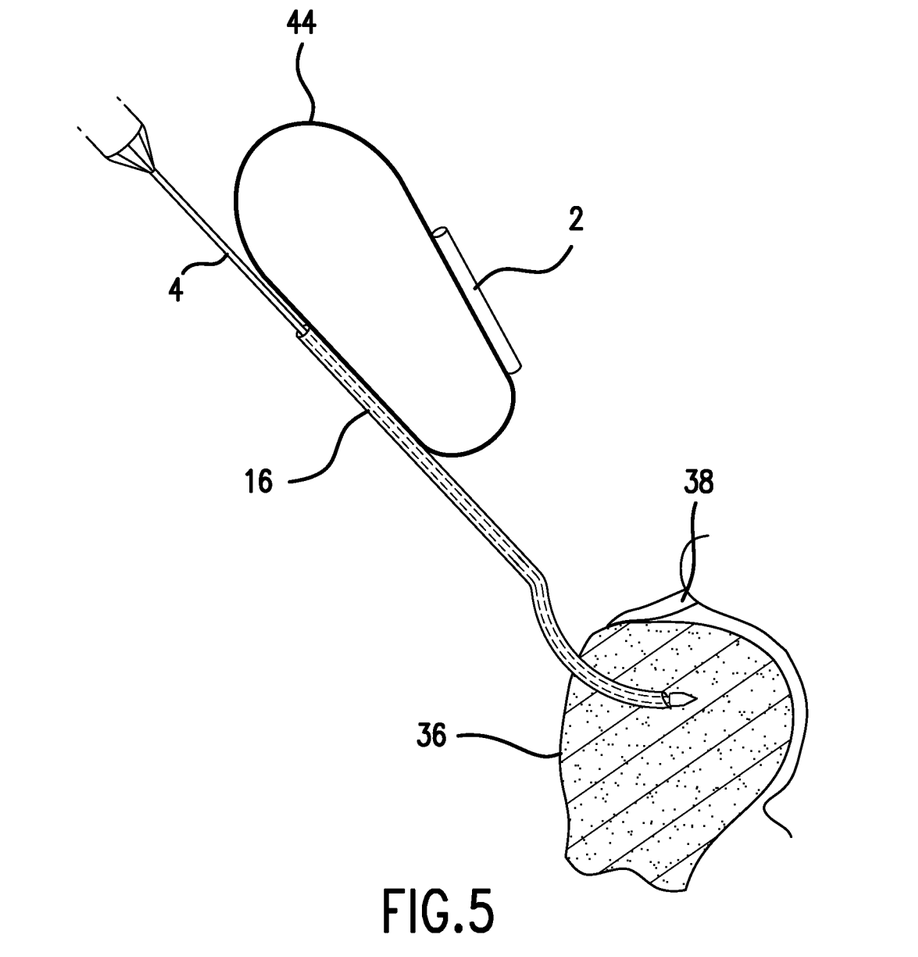
FIG. 5 illustrates insertion of the arcuate lumen rotator cuff drill guide leading with the stylus.

Referring now to the drawings there is shown in FIG. 2 and FIG. 3, a preferred embodiment of the invention demonstrating repairing a rotator cuff. Two arthroscopic portals 30, 32 are formed in the shoulder 34, such as by a scalpel. The humeral head 36 and rotator cuff tendons 38 are present. A curved or arcuate drill guide 16 having a central lumen is inserted into one of the portals, as shown in FIG. 5. The use of the arcuate drill guide is important in rotator cuff repair to miss neurovascular structures and avoid the acromion. The resulting curved tunnel also transfers biomechanical forces placed on the sutures over a radius of bone to minimize stress points on bone and suture alike. If required, cortical bone may be removed prior to insertion of the arcuate drill guide.

Figure 4A:
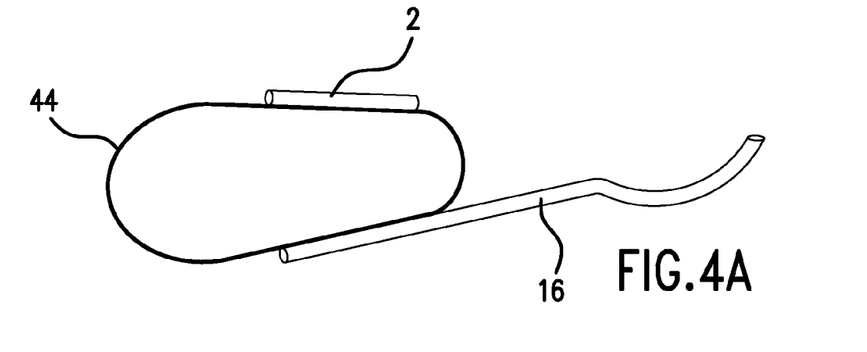
FIG. 4A shows an embodiment of a preferred drill guide assembly of the present invention having an arcuate drill guide, a straight drill guide and a handle.
Figure 4B:
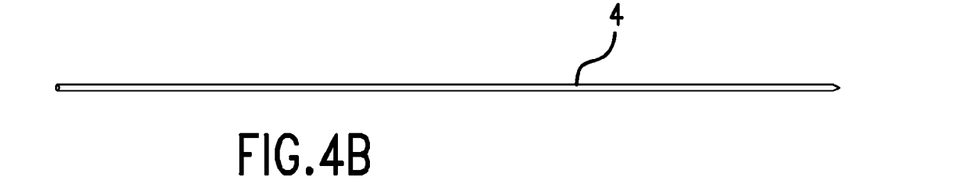
FIG. 4B is a stylus for use in the arcuate drill guide having a central lumen.
Figure 6:
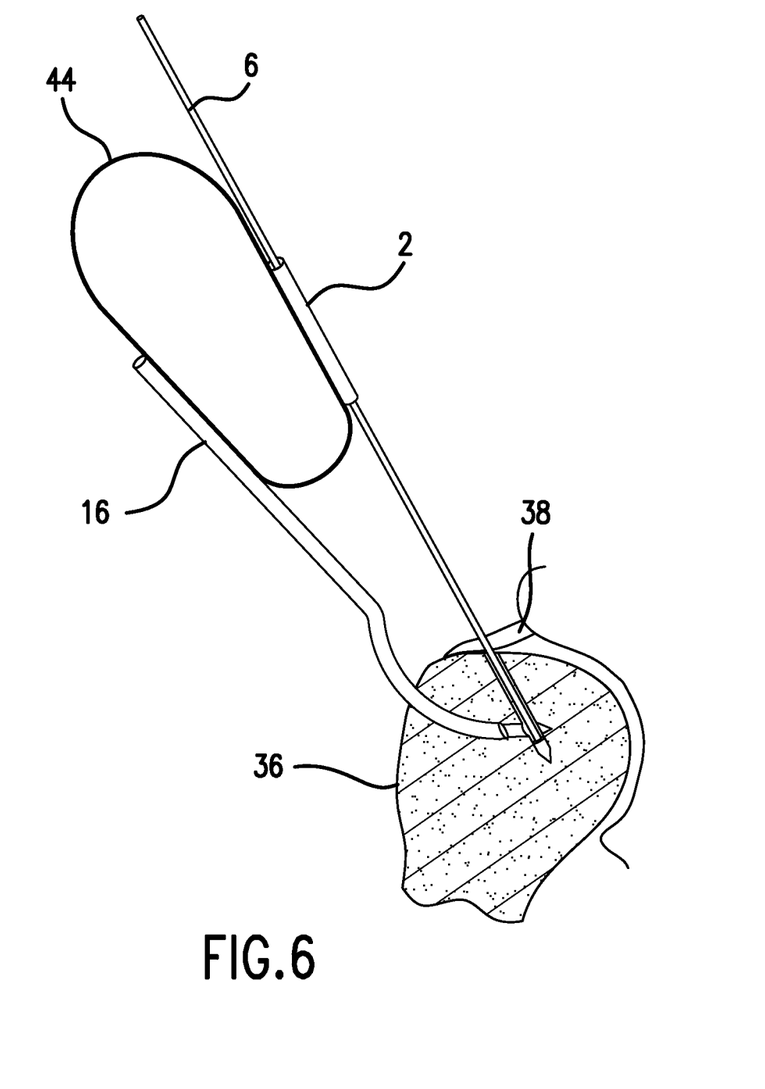
FIG. 6 illustrates the trephine guide pin that has been passed through the straight drill guide lumen.

The central lumen of the arcuate drill guide 16 has a protruding flexible stylus 4 therein that is advanced into the humeral head lateral of, or through, the torn rotator cuff. The stylus 4, shown in FIG. 4B, is formed of a memory retaining material, such as nitinol. The stylus may have a cutter formed in an end thereof, such as a drill or mill type cutter. In the embodiment shown in FIG. 4A, the forward end of the arcuate drill guide 16 is curved. Advancement of the arcuate drill guide 16 may be by manual pressure or by assisted manual force using, for example, a mallet, or by a power tool, such as a drill. The arcuate drill guide forms an arcuate tunnel in the bone. After the arcuate drill guide 16 is fully advanced, the stylus is withdrawn, leaving a small void in the bone that is present beyond the leading edge of the arcuate drill guide as shown in FIG. 5 and FIG. 6.

Figure 1:
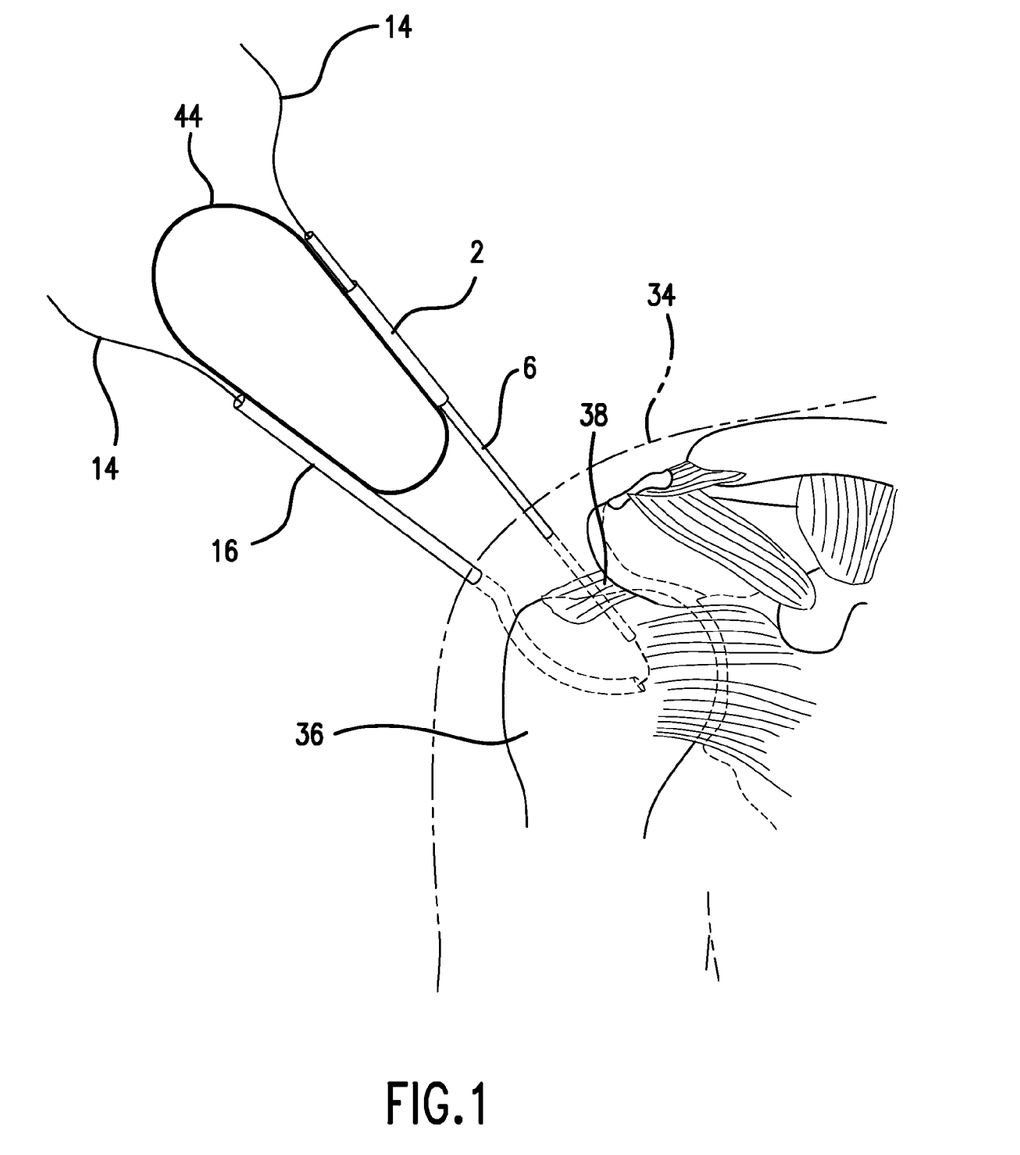
FIG. 1 illustrates a rotator cuff drill guide of the present invention in place with a trephine piercing a torn rotator cuff wherein a single stand of suture is shown passing through the drill guide, rotator cuff tissue, into and out of the humeral head, and exiting the central lumen of the trephine.
Figure 4C:
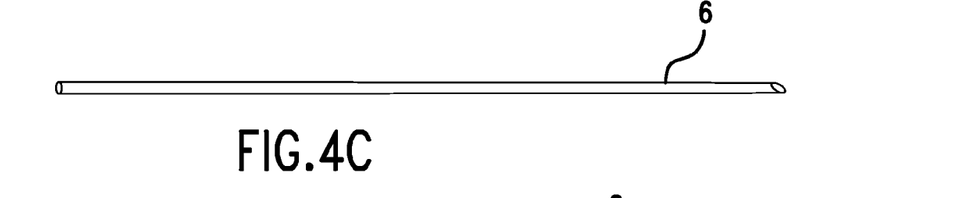
FIG. 4C is a trephine guide pin that fits into the straight drill guide lumen with enough clearance for the trephine.

As shown in FIG. 1, straight drill guide 2 is used to guide instruments through the other portal, i.e., the superior portal. The straight drill guide 2 has a lumen therein. A trephine guide pin 6 is positioned within this lumen. The guide pin may be formed of nitinol, stainless steel, or other materials well know to those skilled in the art. Sufficient space is present within the drill guide lumen for placement of the trephine guide pin 6 (shown in FIG. 4C), so that the guide pin has a sloppy fit within the drill guide. Not shown in FIG. 1 is where some rotator cuff tears would allow the curved portion of the guide 16 to also pierce the rotator cuff to achieve two suture fixation points and thus a stronger repair.

Some tears will allow neither the trephine pin 6, 8 or arcuate guide 16 to pierce the rotator cuff. A separate instrument such as a knot passer, shown in FIG. 13 and FIG. 15 or a suture passer known to those skilled in the art may be needed to pierce dysfunctional tissue.

Figure 4D:
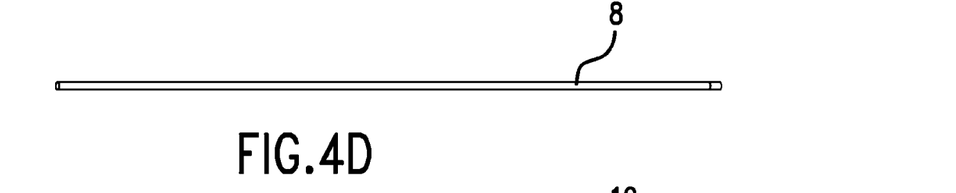
FIG. 4D is an arthroscopic trephine.
Figure 7:
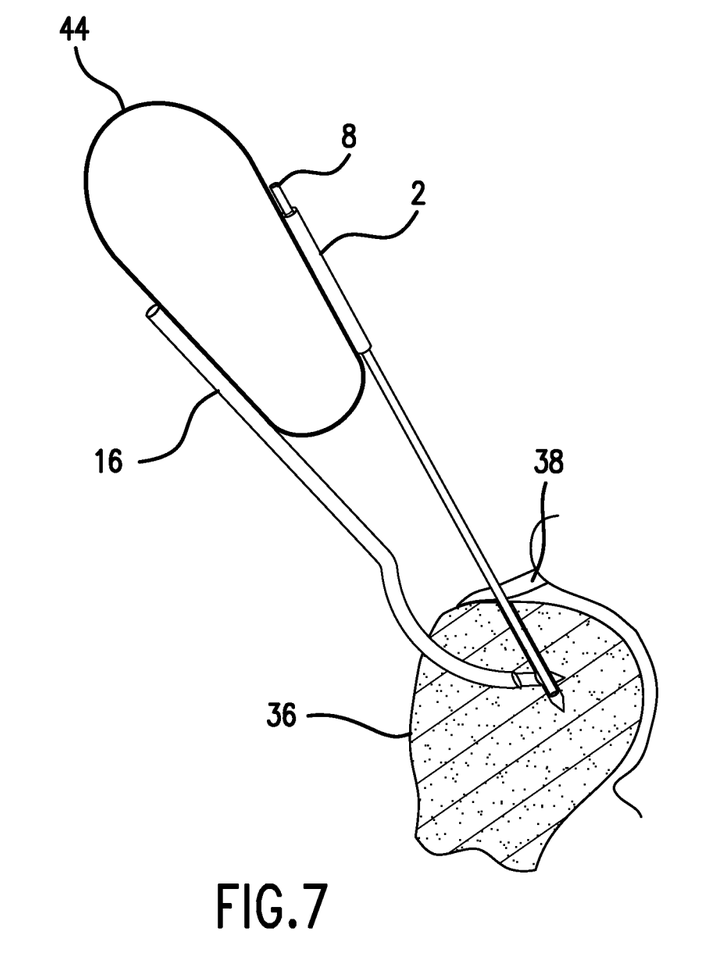
FIG. 7 illustrates the trephine inserted to a calibration point that advances the tip past the bone void left by the trephines guide pin.

The trephine 8, shown in FIG. 4D, is inserted through the lumen of straight drill guide 2. The trephine 8 has a larger diameter than the trephine guide pin 6, but will rotate within the lumen. The trephine 8 enlarges the tunnel, and is moved past the arcuate shaped tunnel formed using the arcuate drill guide 16 as shown most clearly in FIG. 7.

Figure 8:
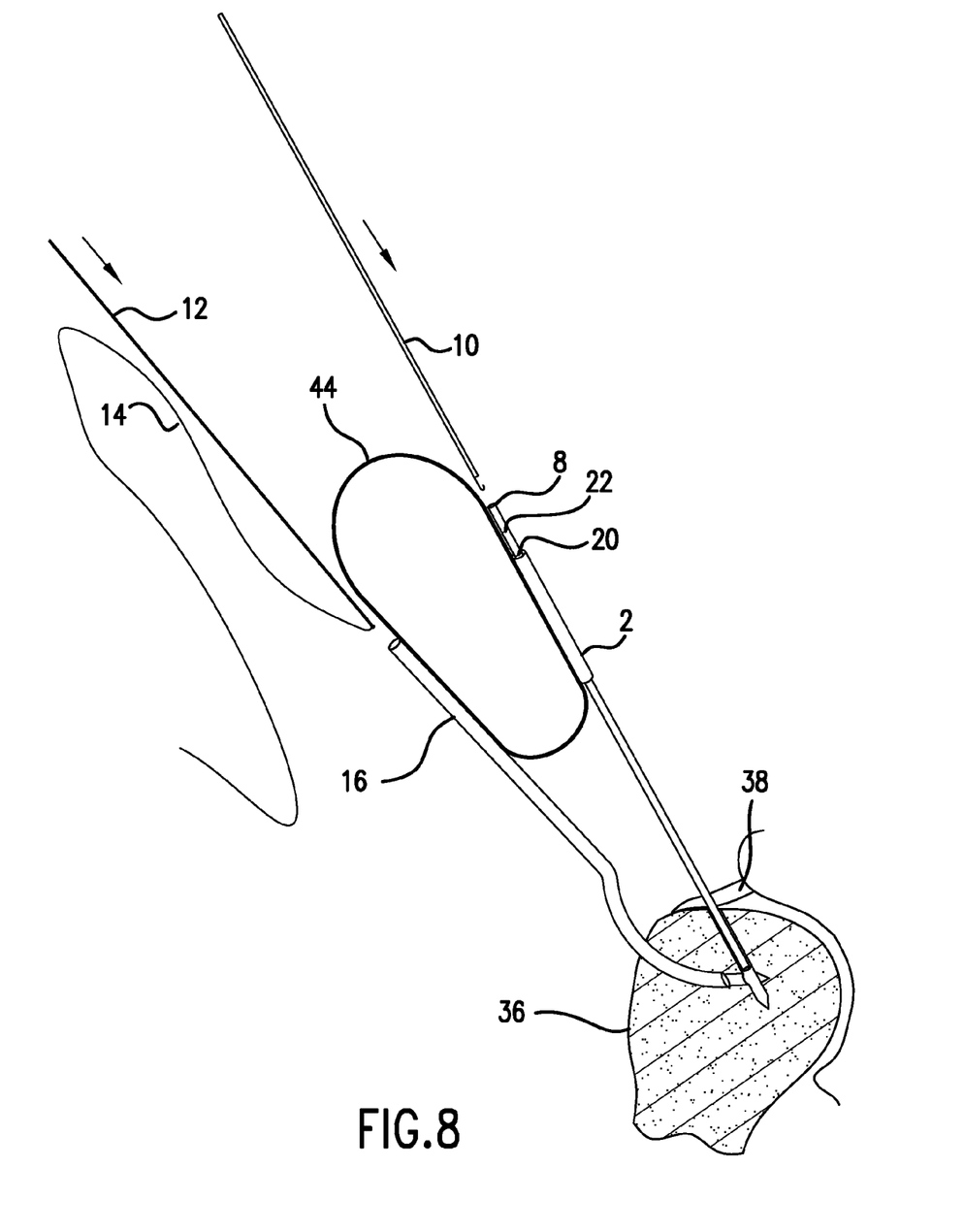
FIG. 8 illustrates the trephine partially retracted to a second calibration mark, the suture stylus with suture being advanced and the hook probe in a readied position.

In operation, the trephine 8 is retracted so that other steps may be performed. For example bone morphogenic proteins or other growth factors may be injected through the lumens. As shown in FIG. 8 the trephine may have calibration marks 20, 22 to indicate the depth of insertion and retraction of the trephine. The bone tunnels intersect/bisect as shown.

Figures 4E, 4F:
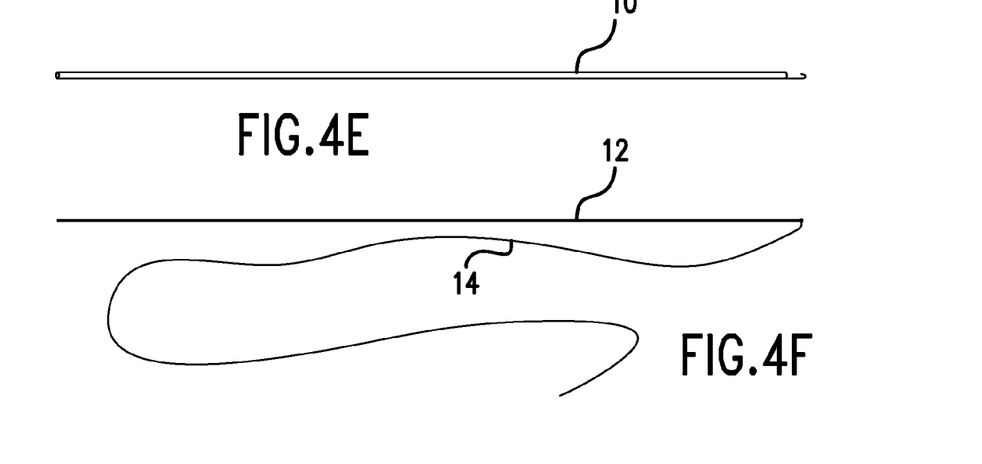
FIG. 4E is an offset hook probe that will pass into the trephine.
FIG. 4F is a suture stylus with suture loosely attached.
Figure 9:
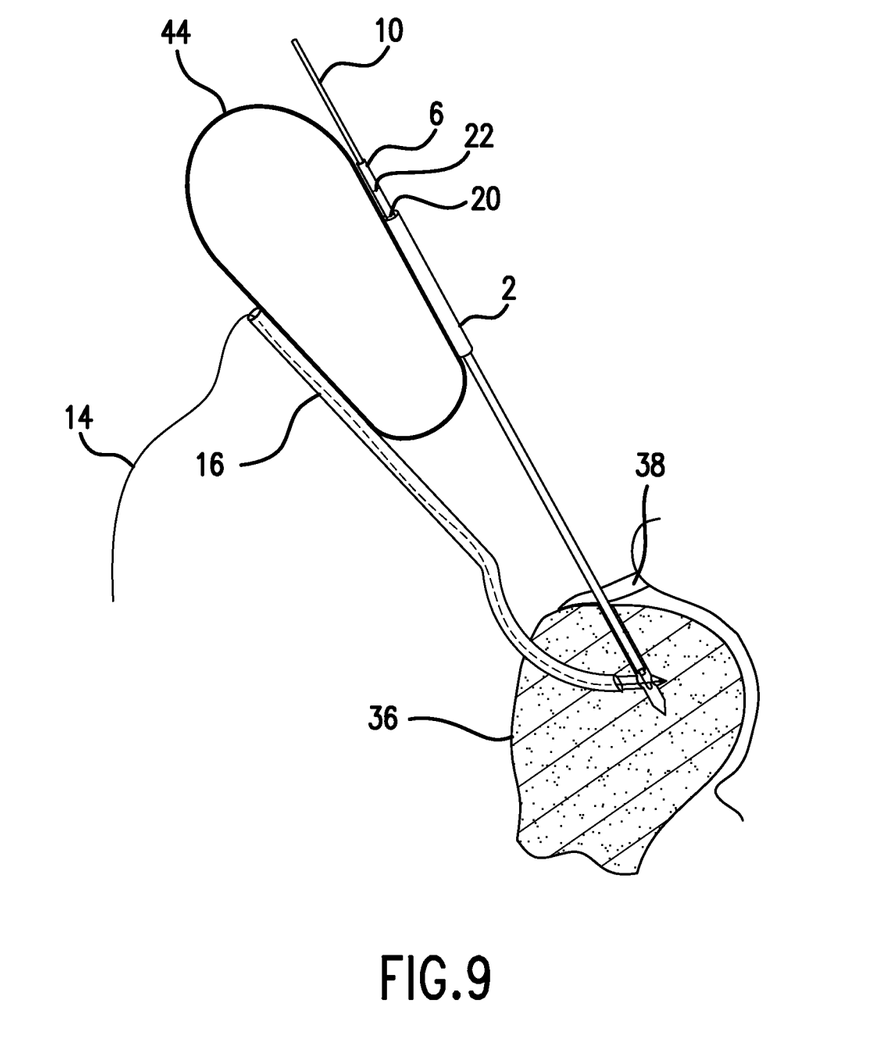
FIG. 9 illustrates the suture lodged in the bone void left by the stylus after being left behind by the suture stylus, and the hook probe which has been passed through the trephine to capture the suture.
Figure 12:
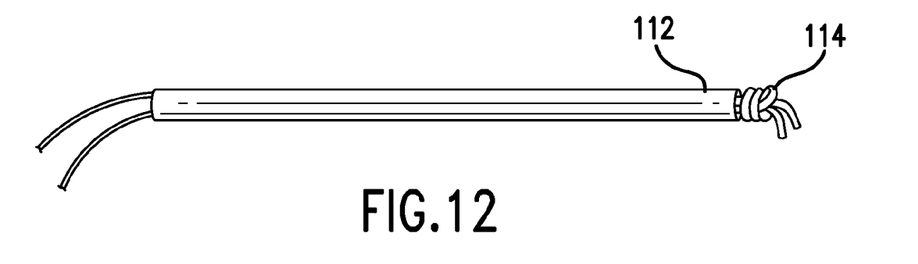
FIG. 12 is an embodiment of a knot pusher for use in the process of the present invention.

With the trephine in place, but with the stylus 4 and the trephine guide pin 6 removed from the drill guides, one or more strands of suture 14 are passed through the lumens of the drill guides, likely converging through a re-approximated rotator cuff tear, and through the two bisecting bone tunnels. The suture also passes through the humeral head (bone), and exits the central lumen. The suture or multiple sutures are advanced through the arcuate drill guide 16 by the suture stylus 12, shown in FIG. 4F or a knot pusher 112. The hook probe 10, shown in FIG. 4E shown in FIG. 12 is inserted through the lumen of the trephine to hook the suture advanced by the suture stylus 12 or knot pusher 112 at approximately the intersection of the tunnels, as shown in FIG. 9. The suture or sutures are advanced past the point of the vacated trephine tunnel.

Removal of the drill guides 2, 16 leaves the suture in place for tying. Multiple suture passes allow for tying of the suture material. For example, three (3) suture passes allow tying three (3) simple stitches 40 as shown in FIG. 2.

FIG. 3 shows two arthroscopic mattress stitches 42 where the initial suture in the center bone tunnel was used to pass two sutures. The two sutures were tied twice with their adjacent sutures to form mattress stitches. Alternatively, the outside suture strands could have been used to pull the corresponding central suture into the outside tunnel, resulting in one less knot left in the patient, and the opportunity to use a sliding knot.

As shown in FIG. 9, the arcuate drill guide 16 and the straight drill guide 2 may be connected by a handle 44. The handle positions the relative angles of the drill guides for forming the tunnels as described. The drill guides are positioned by the handle so that intersecting/bisecting tunnels are formed as disclosed herein. Both drill guides could be straight, with the drill guides angled in a non-parallel fashion to form intersecting/bisecting tunnels. The handle may also be used to receive and transfer a force for advancing the drill guides, such as by striking the handle with a mallet.

Benefits of the present invention over the use of suture anchors include the introduction of minimal foreign material in the patient, a larger "healing footprint" (which is variable with the distance between lumens) and the use of lumens as injection ports for plate rich/poor blood/growth factors or other growth factors. This method of arthroscopic bone/suture tunnel creation also has applications in shoulder laberal repair and posterior cruciate ligament and anterior cruciate ligament repair, without, or at least reducing, the requirement of suture anchors, staples or screws. The geometry of the apparatus relates to an arthroscopic creation of bone tunnels and simultaneous suture passing to repair a torn or partially torn rotator cuff.

Figure 10:
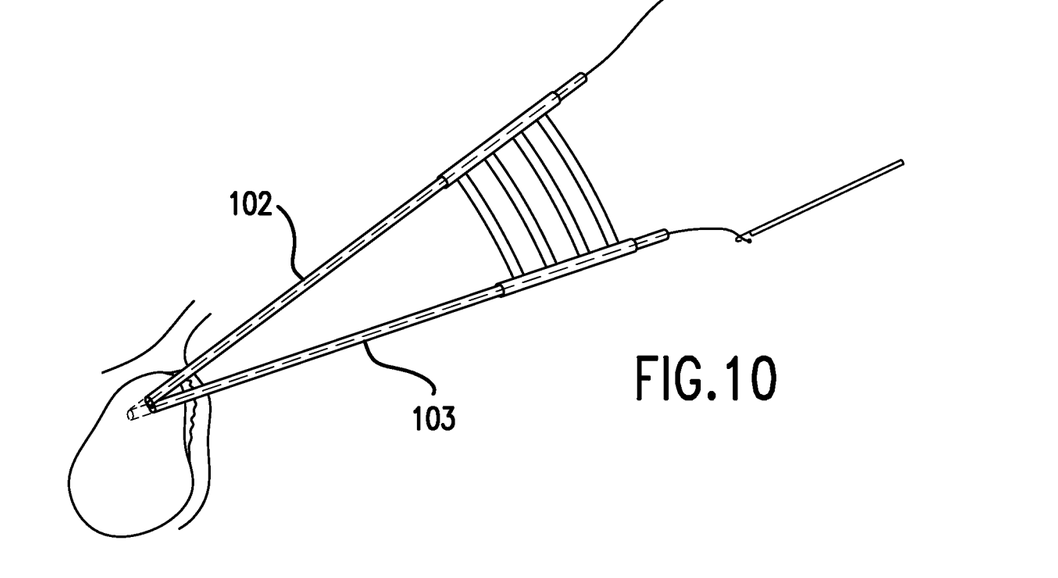
FIG. 10 demonstrates an embodiment of the device using straight, but non-parallel drill guides.

FIG. 10 shows an alternative embodiment of the present invention wherein the method of arthroscopic attachment of tissue to bone uses a different drill guide configuration to address the anatomic structure of the genohumeral joint, which are different that rotator cuff repair. FIG. 10 shows parallel drill guide lumens 102, 103 that are useful for superior labrum deficiencies or tears.

Figure 11:
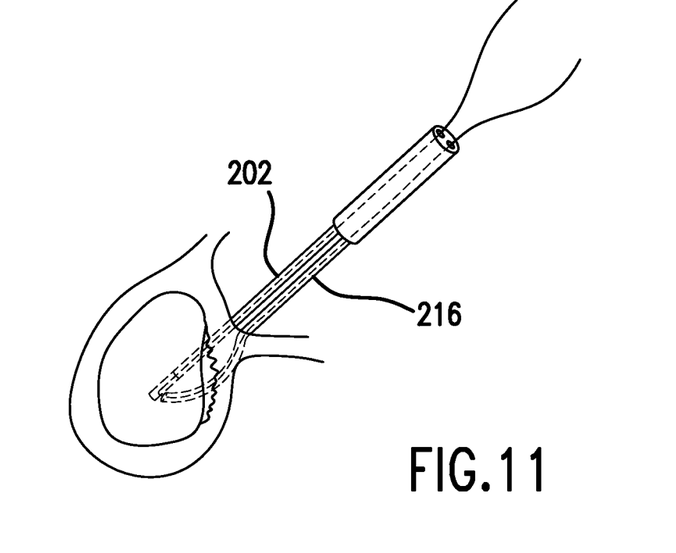
FIG. 11 demonstrates an embodiment of the device showing an additional configuration of an arcuate drill guide.

FIG. 11 shows yet another embodiment of the present invention having a drill guide that is similar to the rotator cuff guide, having one arcuate lumen 216 and one straight lumen 202 but having a different converging angle for inferior laberal repair. Aside from these differences in the apparatus, the method of arthroscopic securing tissue to the glenoid is the same as described for attaching the rotator cuff to the humeral head.

As an alternative to using the suture stylus shown in FIG. 4, there is shown in FIG. 12 a hollow tube or as is more preferably known, a knot pusher 112, of small diameter. The knot passer 112 contains a single strand or multiple strands of suture material having an enlarged end, such as a knot 114, threaded through the central lumen. As is apparent to those skilled in the art, the knot passer may be made of a rigid or flexible material. A knot 114 at the distal end of the strand or strands allows the suture to be passed into position. The tube 112 can be removed and the suture can be left behind as with the stylus of FIG. 4 or the tube 112 can be used to provide improved tactile feedback when contacting the hook probe 10, plus a means of suture protection. The suture 114 can be left in place where it is captured by a hook probe, such as shown in FIG. 4E and FIG. 9 or other suitable means known to those skilled in the art, such as a loop. The hook probe or other instrument may be in place prior to inserting the tube 112 to engage the knot/tube junction and withdraw the suture (s) from the tube.

Figure 13:
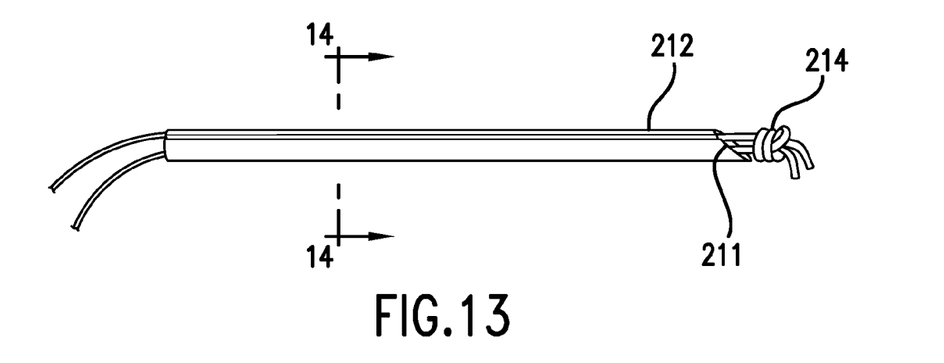
FIG. 13 is an embodiment of a knot passer having a modified distal tip and an inner knot pusher.
Figure 14:
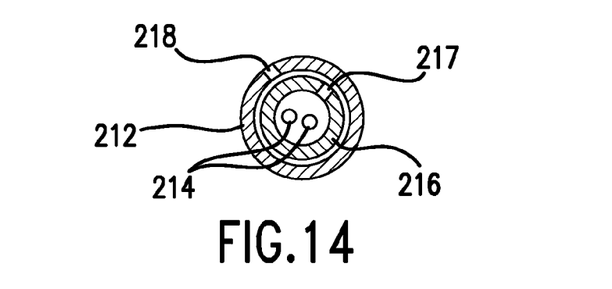
FIG. 14 is across-sectional view of the knot passer of FIG. 13 taken along line 14-14 thereof.
Figure 15:
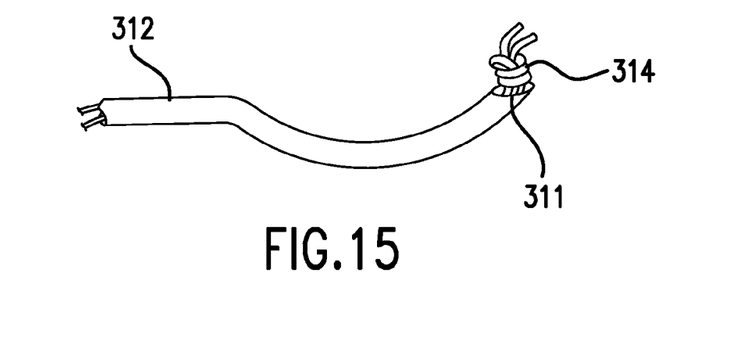
FIG. 15 is another embodiment of a knot passer having modified distal end.

FIG. 13 is an embodiment of a knot passer 212 having a modified distal tip 211 and as shown more clearly in FIG. 14, an inner knot pusher 216 having a smaller diameter that knot passer 212. This would be used to pass sutures through the tissue when neither the trephine or arcuate guide cannot reach dysfunctional tissue. The knot passer 212 contains a single strand or multiple strands of sutures 214, threaded through the central lumen. A knot formed at the distal end of the strand or strands 214 allows the suture to be pushed into position. The knot passer tip 211 may be angled to form a shape point. The knot passer 212 tube has a slot 218 running the longitudinal length of the tube as shown in FIG. 14. In a like manner, the inner knot pusher 216 has a slot 217 running the longitudinal length. When the knot passer and the inner knot pusher are rotated the slots 217, 218 are aligned so that the device may be easily removed from the sutures. In FIG. 15 there is show another modified knot passer 312 having a modified distal end 311 herein the end is curved.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A drill guide assembly for an arthroscopic fixation of tissue to bone using sutures, comprising:
    an arcuate drill guide;
    an arcuate lumen centrally located inside the arcuate drill guide, wherein the arcuate lumen has a protruding flexible stylus that is advanced into the humeral head lateral of the rotator cuff forming an arcuate tunnel in the bone;
    a straight drill guide;
    a straight lumen positioned in the straight drill guide forming a straight tunnel in the bone; and
    a handle connecting the arcuate drill guide to the straight drill guide, wherein the arcuate tunnel and the straight tunnel intersect.

2. The drill guide assembly for an arthroscopic fixation of tissue to bone using sutures as described in claim 1, further comprising a knot pusher sufficiently large to accommodate a suture having an enlarged distal end.

3. The drill guide assembly for an arthroscopic fixation of tissue to bone using sutures as described in claim 2, wherein said distal end of said knot passer has a generally sharp tip.

4. The drill guide assembly for an arthroscopic fixation of tissue to bone using sutures as described in claim 2, wherein said knot passer comprises an inner knot pusher within the lumen of said knot passer, and further comprises a longitudinal slot through the length of both of said knot passer and said inner knot pusher.

5. The drill guide assembly for an arthroscopic fixation of tissue to bone using sutures according to claim 2, wherein said distal end of said knot passer is curved.

6. The drill guide assembly of claim 1, wherein the handle, when struck by a mallet, receives and transfers a force that advances the drill guides.

7. The drill guide assembly of claim 1, wherein the handle is operable to position the relative angles of the drill guides for forming the tunnels.

8. The drill guide assembly of claim 1, wherein the handle is operable to position the drill guides so that intersecting or bisecting tunnels are formed.

9. The drill guide assembly of claim 1, wherein the arcuate drill guide is not the straight drill guide.

10. The drill guide assembly of claim 1, wherein a handle end of the arcuate drill guide contacts the handle, and a handle end of the straight drill guide contacts the handle, without the handle end of the arcuate drill guide contacting the handle end of the straight drill guide.

* * * * *